(12) United States Patent
Klint

(10) Patent No.: US 8,721,625 B2
(45) Date of Patent: May 13, 2014

(54) ENDOVASCULAR MEDICAL DEVICE WITH PLURALITY OF WIRES

(75) Inventor: Henrik Sønderskov Klint, Lyngby (DK)

(73) Assignee: Cook Medical Technologies LLC, Bloomington, IN (US)

( * ) Notice: Subject to any disclaimer, the term of this patent is extended or adjusted under 35 U.S.C. 154(b) by 1389 days.

(21) Appl. No.: 11/314,541

(22) Filed: Dec. 21, 2005

(65) Prior Publication Data
US 2006/0100602 A1    May 11, 2006

Related U.S. Application Data

(62) Division of application No. 10/615,314, filed on Jul. 7, 2003, now Pat. No. 7,025,758, which is a division of application No. 09/770,417, filed on Jan. 26, 2001, now Pat. No. 6,589,227.

(51) Int. Cl.
*A61M 25/00* (2006.01)
*A61M 29/00* (2006.01)

(52) U.S. Cl.
USPC ............ 604/524; 604/523; 600/434; 600/585; 606/200

(58) Field of Classification Search
CPC ................ A61B 2017/1205; A61B 17/12113; A61B 2017/00867; A61B 17/12063; A61B 17/12109; A61B 17/12122; A61B 17/1214
USPC ............ 606/213, 200; 604/524; 600/434, 585
See application file for complete search history.

(56) References Cited

U.S. PATENT DOCUMENTS

| | | |
|---|---|---|
| 3,690,671 A | 9/1972 | Slutsky |
| 4,003,369 A | 1/1977 | Heilman et al. |
| 4,512,338 A | 4/1985 | Balko et al. |
| 4,548,206 A | 10/1985 | Osborne |
| 4,619,274 A | 10/1986 | Morrison |
| 4,748,986 A | 6/1988 | Morrison et al. |
| 4,830,023 A | 5/1989 | De Toledo et al. |
| 4,909,789 A | 3/1990 | Taguchi et al. |
| 4,917,102 A | 4/1990 | Miller et al. |
| 4,932,419 A | 6/1990 | de Toledo |
| 4,934,380 A | 6/1990 | de Toledo |

(Continued)

FOREIGN PATENT DOCUMENTS

| | | |
|---|---|---|
| DE | 3641935 | 6/1987 |
| DE | 29518932 | 8/1996 |
| WO | 9406503 | 3/1994 |
| WO | 9411051 | 5/1994 |

*Primary Examiner* — Darwin Erezo
*Assistant Examiner* — Michael Mendoza
(74) *Attorney, Agent, or Firm* — Brinks Gilson & Lione

(57) ABSTRACT

An endovascular device (1, 100, 200, 300) having a distal end (2), a proximal end (4) and a body portion (3) therebetween. The body portion is made of a multiple filament helically wound row (A) of wires (5), provided with a sealing coating (14) on the inside surface or the outside surface or both. The device may be a catheter (1), a sheath, an introducer, a delivery device, a pusher (100), an embolization coil delivery device (300), or a receptacle (208) for an expandable prosthesis (220) used with a delivery device (200). From 2 to 12, and preferably from 4 to 8, wires (5) are used in the row, and fewer wires may be used proceeding toward the distal end (2) for greater flexibility. The helically wound row of wires transmits torque and provides pushability to the device while resisting kinking, and enables a small outside diameter for reaching very small vessels and extending through very tortuous vessels.

9 Claims, 11 Drawing Sheets

(56) References Cited

U.S. PATENT DOCUMENTS

| | | | | |
|---|---|---|---|---|
| 4,951,677 A | * | 8/1990 | Crowley et al. | 600/463 |
| 4,994,069 A | | 2/1991 | Ritchart et al. | |
| 5,037,404 A | | 8/1991 | Gold et al. | |
| 5,040,543 A | | 8/1991 | Badera et al. | |
| 5,069,217 A | | 12/1991 | Fleischhacker, Jr. | |
| 5,108,407 A | | 4/1992 | Geremia et al. | |
| 5,122,136 A | | 6/1992 | Guglielmi et al. | |
| 5,131,406 A | | 7/1992 | Kaltenbach | |
| 5,171,383 A | | 12/1992 | Sagae et al. | |
| 5,178,158 A | | 1/1993 | de Toledo | |
| 5,184,621 A | | 2/1993 | Vogel et al. | |
| 5,184,627 A | | 2/1993 | de Toledo | |
| 5,211,636 A | * | 5/1993 | Mische | 604/264 |
| 5,217,484 A | | 6/1993 | Marks | |
| 5,224,953 A | | 7/1993 | Morgentaler | |
| 5,226,911 A | | 7/1993 | Chee et al. | |
| 5,228,453 A | | 7/1993 | Sepetka | |
| 5,234,003 A | | 8/1993 | Hall | |
| 5,234,437 A | | 8/1993 | Sepetka | |
| 5,238,004 A | | 8/1993 | Sahatjian et al. | |
| 5,243,996 A | | 9/1993 | Hall | |
| 5,250,071 A | | 10/1993 | Palermo | |
| 5,304,194 A | | 4/1994 | Chee et al. | |
| 5,312,415 A | | 5/1994 | Palermo | |
| 5,318,525 A | | 6/1994 | West et al. | |
| 5,354,295 A | | 10/1994 | Guglielmi et al. | |
| 5,370,685 A | | 12/1994 | Stevens | |
| 5,373,619 A | | 12/1994 | Fleischhacker et al. | |
| 5,376,083 A | | 12/1994 | Mische | |
| 5,382,259 A | | 1/1995 | Phelps et al. | |
| 5,411,476 A | | 5/1995 | Abrams et al. | |
| 5,411,545 A | * | 5/1995 | Breyen et al. | 607/122 |
| 5,419,339 A | | 5/1995 | Palmer | |
| 5,421,338 A | * | 6/1995 | Crowley et al. | 600/463 |
| 5,423,829 A | * | 6/1995 | Pham et al. | 606/108 |
| 5,465,732 A | * | 11/1995 | Abele | 600/585 |
| 5,488,959 A | | 2/1996 | Ales | |
| 5,522,822 A | | 6/1996 | Phelps et al. | |
| 5,546,948 A | | 8/1996 | Hamm et al. | |
| 5,573,520 A | | 11/1996 | Schwartz et al. | |
| 5,605,162 A | | 2/1997 | Mirzaee et al. | |
| 5,643,278 A | | 7/1997 | Wijay | |
| 5,643,339 A | | 7/1997 | Kavteladze et al. | |
| 5,645,064 A | | 7/1997 | Littmann et al. | |
| 5,653,684 A | | 8/1997 | Laptewicz et al. | |
| 5,683,451 A | | 11/1997 | Lenker et al. | |
| 5,690,666 A | | 11/1997 | Berenstein et al. | |
| 5,695,483 A | | 12/1997 | Samson | |
| 5,702,373 A | | 12/1997 | Samson | |
| 5,720,300 A | | 2/1998 | Fagan et al. | |
| 5,725,534 A | | 3/1998 | Rasmussen | |
| 5,733,400 A | | 3/1998 | Gore et al. | |
| 5,741,429 A | | 4/1998 | Donadio, III et al. | |
| 5,749,894 A | * | 5/1998 | Engelson | 606/213 |
| 5,749,919 A | | 5/1998 | Blanc | |
| 5,759,161 A | | 6/1998 | Ogawa et al. | |
| 5,780,455 A | | 7/1998 | Brenner et al. | |
| 5,797,953 A | | 8/1998 | Tekulve | |
| 5,800,455 A | | 9/1998 | Palermo et al. | |
| 5,814,062 A | | 9/1998 | Sepetka et al. | |
| 5,824,041 A | | 10/1998 | Lenker et al. | |
| 5,827,201 A | | 10/1998 | Samson et al. | |
| 5,843,092 A | | 12/1998 | Heller et al. | |
| 5,843,924 A | | 12/1998 | Brenner et al. | |
| 5,897,819 A | | 4/1999 | Miyata et al. | |
| 5,910,364 A | | 6/1999 | Miyata et al. | |
| 5,914,323 A | | 6/1999 | Brenner et al. | |
| 5,947,940 A | | 9/1999 | Beisel | |
| 5,957,940 A | | 9/1999 | Tanner et al. | |
| 5,984,877 A | | 11/1999 | Fleischhacker, Jr. | |
| 5,993,424 A | | 11/1999 | Lorenzo et al. | |
| 5,994,647 A | | 11/1999 | Avellanet | |
| 5,997,487 A | | 12/1999 | Kolehmainen et al. | |
| 6,019,736 A | | 2/2000 | Avellanet et al. | |
| 6,024,763 A | | 2/2000 | Lenker et al. | |
| 6,027,461 A | | 2/2000 | Walker et al. | |
| 6,027,863 A | | 2/2000 | Donadio, III | |
| 6,066,155 A | | 5/2000 | Amann et al. | |
| 6,107,004 A | | 8/2000 | Donadio, III | |
| 6,117,157 A | | 9/2000 | Tekulve | |
| 6,126,685 A | | 10/2000 | Lenker et al. | |
| 6,159,206 A | * | 12/2000 | Ogawa | 606/32 |
| 6,165,198 A | * | 12/2000 | McGurk et al. | 606/200 |
| 6,193,728 B1 | * | 2/2001 | Ken et al. | 606/108 |
| 6,238,415 B1 | | 5/2001 | Sepetka et al. | |
| 6,312,454 B1 | | 11/2001 | Stockel et al. | |
| 6,348,041 B1 | | 2/2002 | Klint | |
| 6,350,278 B1 | | 2/2002 | Lenker et al. | |
| 6,355,060 B1 | | 3/2002 | Lenker et al. | |
| 6,383,146 B1 | | 5/2002 | Klint | |
| 6,458,092 B1 | | 10/2002 | Gambale et al. | |
| 6,458,137 B1 | | 10/2002 | Klint | |
| 6,589,227 B2 | | 7/2003 | Klint | |
| 6,689,120 B1 | | 2/2004 | Gerdts | |
| 6,776,788 B1 | | 8/2004 | Klint et al. | |
| 6,849,081 B2 | | 2/2005 | Sepetka et al. | |
| 2004/0186491 A1 | | 9/2004 | Klint et al. | |
| 2005/0154417 A1 | | 7/2005 | Sepetka et al. | |

* cited by examiner

ENDOVASCULAR MEDICAL DEVICE WITH PLURALITY OF WIRES

CROSS-REFERENCE TO RELATED APPLICATIONS

This application is a divisional of application Ser. No. 10/615,314 now U.S. Pat. No. 7,025,758, which was filed on Jul. 7, 2003 as a divisional of application Ser. No 09/770,417, filed on Jan. 26, 2001 and issued into U.S. Pat. No. 6,589,227.

This application claims priority of the following European applications:
Serial No. 00610012.7 filed Jan. 28, 2000
Serial No. 00610013.5 filed Jan. 28, 2000
Serial No 00610014.3 filed Jan. 28, 2000
Serial No. 00610015.0 filed Jan. 28, 2000

TECHNICAL FIELD

The present invention relates to the field of medical devices and more particularly to vascular devices such as catheters and delivery systems for implantable devices.

BACKGROUND OF THE INVENTION

Catheters for medical diagnostic or therapeutic use are well known. A catheter has a distal end and a proximal end, with a body extending therebetween and a lumen extending therethrough from end to end. A wide variety of catheters exists for percutaneous insertion by the Seldinger technique into the vascular system to accomplish diagnostic or therapeutic objectives. The vessels of the peripheral vasculature have a relatively large diameter and low tortuosity, the coronary vasculature is somewhat smaller and more tortuous, and the vasculature in the soft tissue of the brain and liver is of small lumen and is very tortuous.

In order to be able to access the various parts of the vasculature, the catheter needs to be flexible and to maintain its column strength when it follows a tortuous path. The contradictory requirements for flexibility and column strength are particularly pronounced in catheters for intracranial catheterizations used in a variety of diagnostic and interventional neurological techniques including delivery of contrast fluids, drugs or a vasoocclusive agent, treatment of tumors, aneurysms, AVS (arteriovenous shunts) and so forth.

When a central member is to be moved within a catheter or sheath to perform an activity at or beyond the distal end of the catheter, after the catheter has been positioned, the central member is to be pushed through the catheter lumen. The more tortuous the path and the smaller the catheter the more difficult it is to advance the central member through the catheter lumen. This difficulty is in particular pronounced in coaxial systems for intracranial use. Where the central member is a delivery device for an embolization coil and must be rotated to disconnect from the coil upon release at the treatment site, the central member must be capable of transmitting torque to its distal end for assured coil disconnection; one such prior art coil delivery system is disclosed in U.S. Pat. No. 5,122,136; but it is a common problem that such prior art coil delivery members have relatively high rigidity which is problematic in small or tortuous vessels with aneurysms. Where the device is a pusher to push a device such as a stent from the distal end of the catheter, the pusher must have substantial column strength as well as great flexibility.

Where a catheter is to be used for delivery of an endovascular prosthesis to a treatment site, such as a stent, a stent graft, a valve member, or a filter, where the prosthesis is compressed to pass through the catheter and then selfexpand upon release therefrom within a body lumen, the prosthesis must be constrained while within the catheter and imposes significant forces against the surrounding catheter body.

It is an objective of the present invention to provide a medical device that includes a distal area that is very flexible and yet easily pushable and capable of transferring torque in an assured, controllable manner.

It is another objective to provide a catheter system that makes it easier to advance the central member through the catheter also in cases where the catheter exhibits sharp turns.

It is further an objective to provide a catheter that resists the substantial radially outward forces of a compressed endovascular prosthesis contained within the distal end thereof, and yet be very flexible and capable of transferring torque.

It is yet another objective to provide a central member for movement within a catheter lumen that is very flexible, has substantial column strength and/or is capable of transferring torque.

BRIEF SUMMARY OF THE INVENTION

The foregoing and other problems are solved and a technical advance is achieved in an illustrative medical device for passage along the vasculature of a patient, having a body portion comprising primarily a plurality of coils or turns of a plurality of wound filaments or wires. The medical device may be a catheter or may be one or more components of a delivery system for endovascular devices, such as a central member within a catheter, for example, a pusher or delivery device for an embolization coil. Two to twelve filaments such as wires, and preferably from four to eight wires, are preferably helically wound adjacent to each other as a group or row with a pitch corresponding generally to the aggregate width of the adjacent wires in the row.

The wound wires transfer torque and also force components directed in the axial direction of the medical device to the distal end thereof, and this construction is found to give a very high resistance to kinking of the medical device. When a catheter according to the present invention is heavily bent, the cross-section of the catheter maintains a circular shape. This provides a distinct advantage over prior art catheters which are deformed into an oval shape in cross-section when bent leading to kinking. The catheter surprisingly maintains its capabilities for transferring torque and push when it follows a tortuous path involving two or more loops, probably because of the excellent kinking resistance. These qualities facilitate placement of the catheter at the desired position in the vascular system, and by making the catheter system so that the inner surface of the catheter is mainly undeformable by a central member moving axially therewithin, it is virtually impossible for the central member to get stuck in the catheter wall, even in situations where the catheter is heavily curved. This is in contrast to prior art coaxial systems where the catheter is made of a soft material such as a resin, the inner surface of which is readily deformable in a local area, causing the formation of a small bead in front of the tip of the central member bearing against the wall of the curved catheter. It is an advantage of the catheter according to the present invention that the wall is primarily made of wires that provide a hard and relatively slippery inner surface resulting in low resistance to advancing the central member through the lumen of the catheter.

The inventive catheter maintains three valuable characteristics of very high flexibility, pushability and torqueability even when set in a very tortuous pattern involving two or more tight loops, and the catheter can thus be of use in very small and distant vessels such as deep brain sites accessed by intracranial catheterization. Preferably, a thin sealing coating of elastic, low-friction material, or adhesive material may be provided over the outwardly directed surfaces of the coiled wires or along the inner surfaces that define a lumen, or at least in recesses between abutting wires or in interstices between nonabutting turns between the groups of wires, thus sealing the interstices between the wires so that the catheter wall is leakproof especially where the device is a catheter or sheath.

Further, wires may have the same diameter in the group and extend the entire length of the device, or the device may have portions with wires of different diameters, lessening toward the distal end and thereby decreasing gradually in outer diameter; the device may also have a noncoiled part in the proximal region such as a supplementary cannula or tubing.

In the present context, the term "catheter" is to be understood in the sense that it can be an ordinary catheter, but also a sheath, which is a short catheter, and in the latter case the central member can be a catheter, e.g., a catheter according to the present invention. The sheath can have a check-flow valve or a fitting at the proximal end in order to stop bleeding out of the puncture site. In one aspect, the catheter may be utilized without a guidewire. When intended for use in a soft tissue region, it is preferred that the distal end of the catheter is provided with a buffer member, such as a soft obturator, that distributes the force from the catheter tip over a large area so that damage to the vascular wall is avoided. The term "central member" can be a member that simply blocks the distal opening of the catheter during inflation of a balloon for percutaneous transluminal coronary angioplasty; it may also be an embolization means such as a sack containing several occlusion coils, or a stent for expansion on a balloon, a sensor body for measuring pressure or temperature or the composition of blood, a physical shunt member, a retrieval wire or a forceps used to retrieve another member from a vascular site; or it can be a central member of some other kind.

In another aspect, the number of wires may vary along the length of the catheter, such as reducing the number of wires in the row during the winding operation in the distal direction, enabling a larger pitch angle and increasing the flexibility of the catheter proximate to the distal end.

In a second embodiment, the medical device may be a delivery system for a prosthesis such as a stent, a stent graft, a valve member, or a filter, wherein the prosthesis is compressible to be placed within a receptacle at the distal end of the delivery catheter and is then radially expandable upon delivery to a treatment site after being urged from receptacle. The delivery system has a catheter shaft with a receptacle that may be simply a distal end portion of the catheter shaft, but the receptacle may also be a separate tubular member that extends from the distal end of the catheter shaft, or optionally partially within the distal end. The receptacle, whether integral with the catheter shaft or a separate member, is primarily defined by a group of wires wound about a lumen, thus having the same advantageous properties of high flexibility and kink resistance as the catheter shaft; optionally and preferably, when the receptacle is a separate member, the catheter shaft may also be of the inventive type hereinbefore set forth. The receptacle may have a larger lumen dimension than the lumen of the catheter shaft, such as by having a smaller wall thickness through use of smaller diameter wire or grinding away an innermost portion of the coiled wires of the distal tip when integral with the catheter shaft, since the wall thickness required for resisting the outward pressure from the radially compacted prosthesis is smaller than the wire thickness required to transmit axial thrust over a long shaft distance, such as 80 cm or more, enabling the outer diameter to remain the same as that of the catheter shaft portion.

In a third embodiment, a prosthesis receptacle is a separate member and is fixed to the helically wound multiple filament row of wires of the catheter shaft, in axial extension thereof. This allows the prosthesis receptacle to be designed and manufactured independently of the shaft portion. The mounting in direct extension of the wire or wires of the catheter shaft makes the prosthesis receptacle follow torsional actions on the shaft portion. Although the prosthesis receptacle can be designed in any manner capable of resisting the outward pressure applied to the inside of the receptacle by the compressed prosthesis, it is preferred that the prosthesis receptacle be a tubular segment of multiple filament construction, such as a braided wire construction providing the prosthesis receptacle with a high flexibility. More preferably, the receptacle is a construction of a second helically wound group or row of multiple wires; this makes it possible to obtain a very diminutive outer diameter as only a single layer of wires is required.

In yet another embodiment, the medical device may be a pusher for use in a delivery system of the type described above, where the pusher is primarily comprised of multiple wires that are helically coiled, resulting in a hollow construction with torqueability and pushability similar to the shaft portion of the delivery device and with slightly greater flexibility due to the smaller outer diameter of the row of wires.

In still another embodiment, the medical device may be used in an introducer for an embolization device, where the delivery member comprises primarily a plurality of wires to provide the advantageous torqueability of the present invention. The distal end of the delivery member thus is able to be rotated from rotation of the proximal end thereof, and thus being disconnectable through unscrewing from the embolization device, a technique that causes only negligible influence on the vasculature while enabling precise maintenance of the embolization device in its desired position during detachment even in very tortuous paths to treatment sites such as intracranial locations.

BRIEF DESCRIPTION OF THE DRAWINGS

Embodiments of the present invention will now be described by way of example with reference to the accompanying drawings, in which.

DETAILED DESCRIPTION OF THE INVENTION

Figure 1:
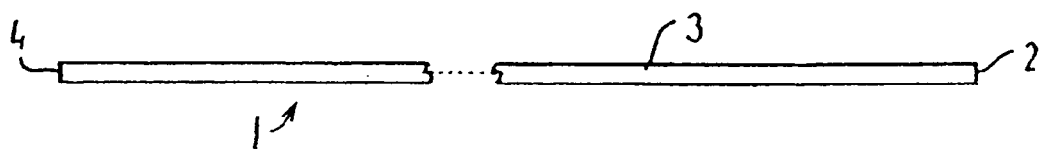
FIG. 1 is a side view of a catheter according to the present invention.

In the following description of the depicted embodiments, the same reference numerals are used for features of the same type. FIGS. 1 to 12 illustrate luminal medical devices such as catheters and sheaths, FIGS. 13 to 18 illustrate prosthesis receptacles and delivery systems therefore; and FIGS. 19 to 27 illustrate embolization device delivery systems.

A vascular medical device according to the present invention and illustrated in FIG. 1 is generally denoted 1, and it has a distal end 2, a body portion 3 extending from the distal end to a proximal end 4. The body portion is made of a first helically wound multiple-filament sequence, group or row of wires 5 and it has a central longitudinally extending lumen 6. The medical device may be a catheter, and a catheter is normally open ended at both the proximal and the distal end; but for special uses such as a single lumen balloon dilatation catheter, the distal end can be provided with means for barring the distal end opening (see FIG. 6).

For example, a catheter according to the present invention can be a balloon dilatation catheter used for percutaneous transluminal coronary angioplasty, an angiography catheter, a drug delivery catheter, a guiding catheter, an infusion catheter, and so forth.

The wires 5 used in the helically wound multifilament group or row are of a linear elastic material, such as stainless steel, titanium or tantalum, or it is made of a superelastic alloy, such as nitinol. Preferably, the wires have an ultimate tensile strength in the range of 1800 to 2700 N/mm.sup.2 but lower or higher values are also possible. The body portion 3 of the catheter is made by placing a group of from two to twelve wires of desired wire diameter in a row next or closely adjacent to each other, whereafter the group of wires is wound according to the desired pitch angle in a common movement into the body portion. Because a row of wires is wound, an individual wire is restricted in movement by the other wires and is plastically deformed into a permanent helical shape which is kept without any further restraints other than the remaining wires in the row. The winding can be done on the inside end of a tubular support member where the row of wires is inserted at said end by rotating and simultaneously pushing the wires against the inside of the support. The wound wire then exits at the other end of the support. This produces a wire body with a very precise outer diameter.

Figure 2:
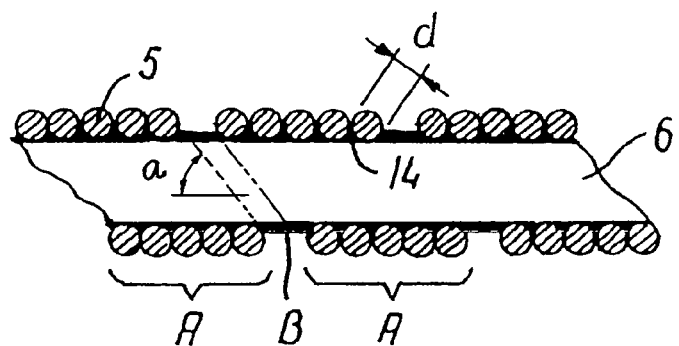
FIGS. 2 and 3 are enlarged partial views in longitudinal section of embodiments of the catheter in FIG. 1.
Figure 7:
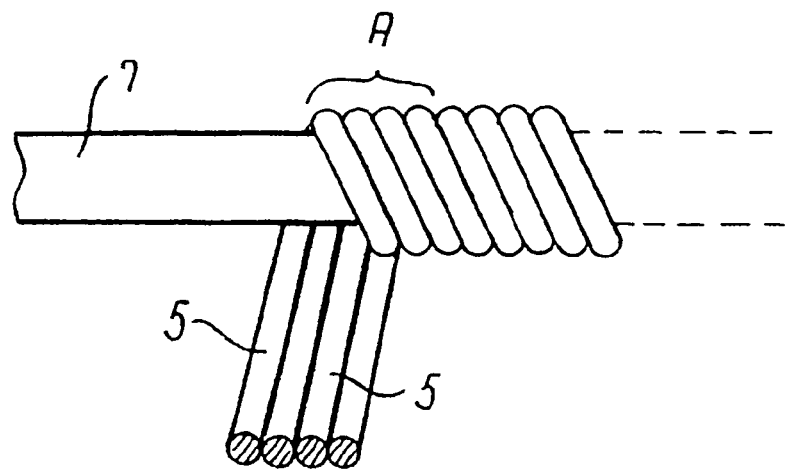
FIG. 7 depicts a winding operation on a multiple-wire row.
Figure 9:
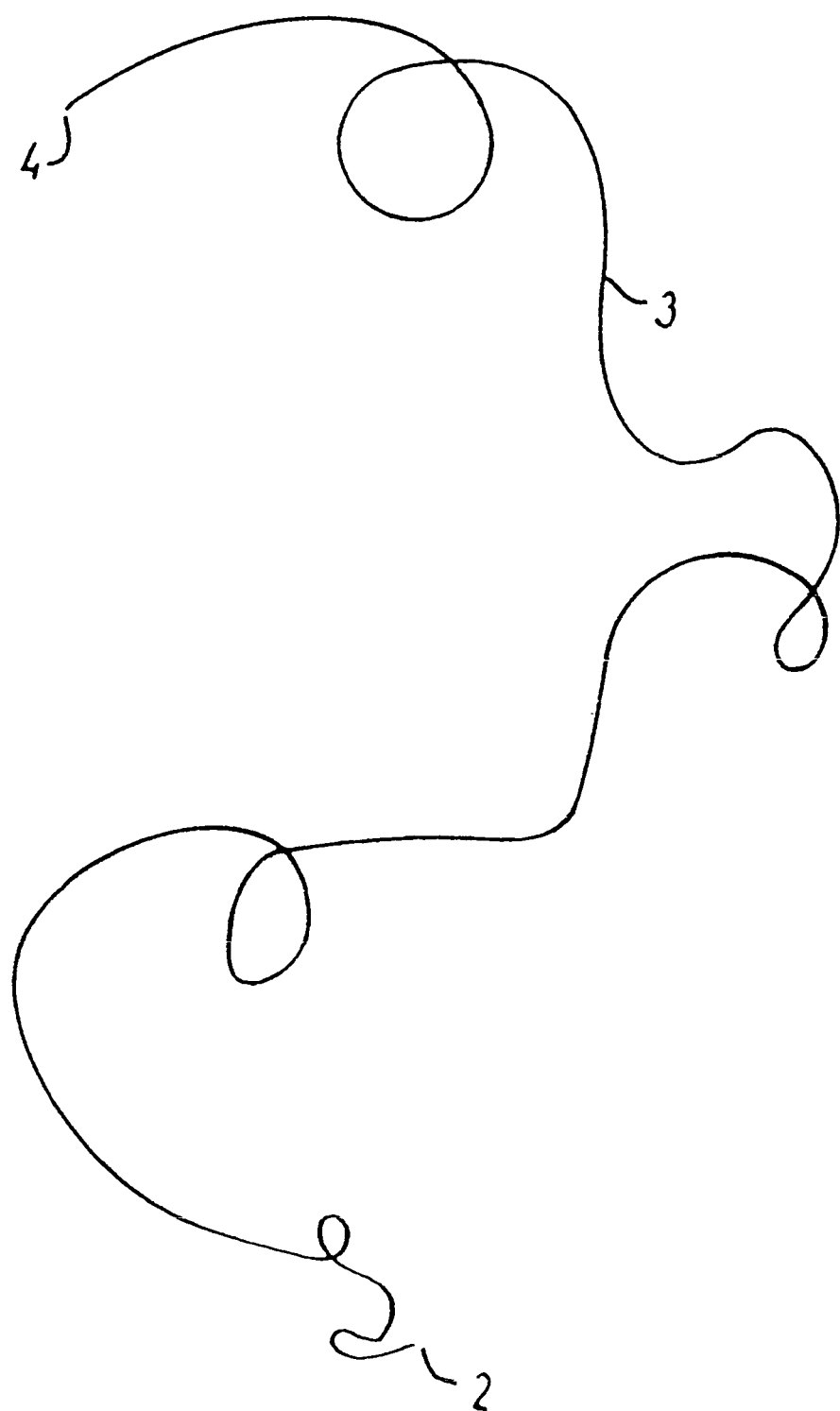
FIG. 9 is an illustration of the catheter of FIG. 1 in position in the vascular system.

Alternatively, the winding operation can take place about a mandrel 7. FIG. 7 depicts a winding of a row A of four identical wires 5. After the winding the mandrel with the coiled wires can be subjected to heat treatment in order to remove residual stresses from the wires. As an example the heat treatment can last for about two hours in an oven at a temperature of about 500° C. Generally, the temperature can be in the range of 400 to 600° C. and the holding time at the temperature can last for many hours, such as up to 20 hours or more. After the heat treatment the mandrel is removed from the wires. The wires in the resulting helically wound multiple-wire group maintain their mutual position even when heavily torqued, bent or pushed, presumably because each single wire is supported by the contiguous wires in the row. The winding operation can be effected so that the windings are touching each other, but preferably it is performed so that an interstice B is present between the turns (FIG. 2). The interstice facilitates bending of the body portion in tight turns along the vasculature such as is shown in FIG. 9.

The size of the pitch angle a (FIG. 2) depends on the diameter of the wires, the diameter of the body portion 3 and the number of wires in the row. The most preferred. pitch angle a for the catheter is in the range of 40° to 68° or 50° to 70°. However, the combination of torque-transferral, pushability and transverse flexibility is normally well-balanced for pitch angles in the range of 50° to 68°. The diameter d of the wire is typically in the range of 0.03 to 0.75 mm, and preferably in the range of 0.15 to 0.45 mm. The present invention includes providing a medical device having different segments wherein the row of wires is set to different pitch angles, or wherein different rows of wires have different pitch angles.

In order to make the tip portion of the catheter more visible on a screen it is desirable to use some kind of radiopaque material, such as platinum or gold. It can be of annular shape and be located at a predetermined distance from the distal end 2, or the terminal end of the distal tip of the catheter can be provided with a marker means for making it radiopaque, such as a gold layer or a gold thread.

The catheter can be made with a uniform diameter throughout its length. In case the catheter has a diminishing diameter towards the distal end, a prefabricated catheter of uniform diameter can be ground to the desired dimensions.

Figure 5:
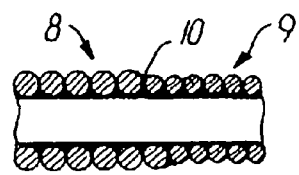
FIG. 5 is an enlarged partial and sectional view of the transition between two catheter segments having wires of different diameter.

As an alternative or supplement to grinding, the catheter can be composed of several segments in which the wires have mutually different diameters and cross-sectional areas. In a proximal segment 8 the wires can have a larger diameter than the wires in a distal segment 9. The segments can be joined together in axial extension by laser welding 10 as depicted in FIG. 5, by soldering, by bracing or in another manner such as mutual geometrically locking of the wires in the segments or by mechanical locking, such as press-fitting one segment into the lumen of the other segment, or binding the segments in axial extension with threads or suture.

When the catheter body is of multi-segment construction, the inner lumens of the segments are preferably of even size which brings the advantage that an advancing guidewire can not snag or grip onto a step in the inner wall of the body portion.

Figure 4:
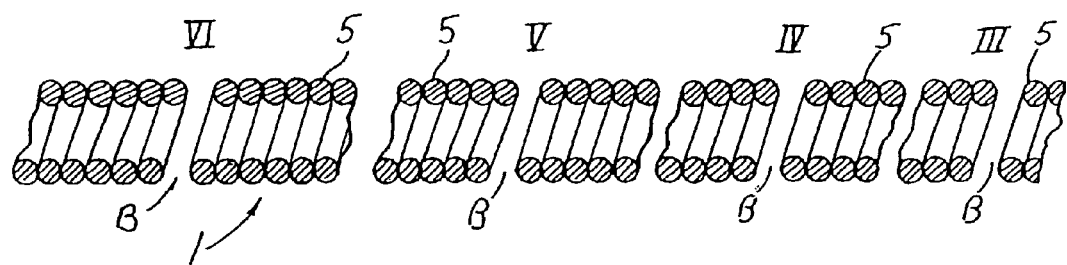
FIG. 4 is a partial view in longitudinal section of an embodiment where the number of wires in a row varies along the length of the catheter.

In the embodiment illustrated in FIG. 4, the number of wires in said helically wound group or row of wires varies along the length of the catheter. During the winding operation the number of wires in the row is reduced one by one at the points in time where the individual segment having a certain number of wires has obtained the desired length. The segment marked "VI" has six wires in the row, and the segments marked "V", "IV" and "III" have five, four and three wires, respectively, in the row. Each time a wire is left out of the row, the pitch gets shorter and the pitch angle grows resulting in an even more flexible consecutive segment. The advantage of this embodiment is that the wires extending into the distal end segment are continuous from the distal end to the proximal end of the catheter, thus avoiding any need for joining the various segments. It is possible to secure the wire ends of the discontinuous wires onto the other wires, such as by welding, soldering or the like.

Figure 8:
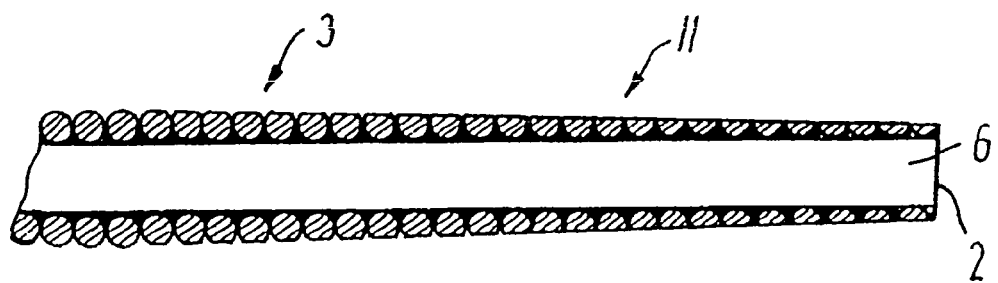
FIG. 8 depicts a catheter segment having decreasing outer diameters.

A grinding procedure can also be used to produce one or more tapered segments 11 in the body portion 3 (FIG. 8). The taper can extend along a substantial length of the body portion. In the tapered segment the outer diameter of the catheter diminishes toward the distal end. Due to the taper, the catheter obtains a gradually increasing transverse flexibility and a higher softness, but column strength and torque are nevertheless surprisingly transferred to the distal end.

Figure 6:
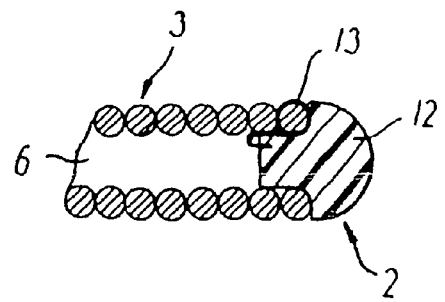
FIG. 6 is an enlarged view of an embodiment having a catheter tip with a buffer member.

When the catheter is to be advanced without a guidewire, the distal end 2 can be provided with a soft buffer 12, as shown in FIG. 6, having a rounded distal end which acts gently on the vascular wall when the catheter is pushed forwardly. A thread 13 can be securely embedded into the soft pliable material of buffer 12 and be ensnared around one of the distal wires, so that the thread will keep the buffer connected to the catheter body portion when the buffer is pushed out and cleared from the lumen of the catheter.

Figure 3:
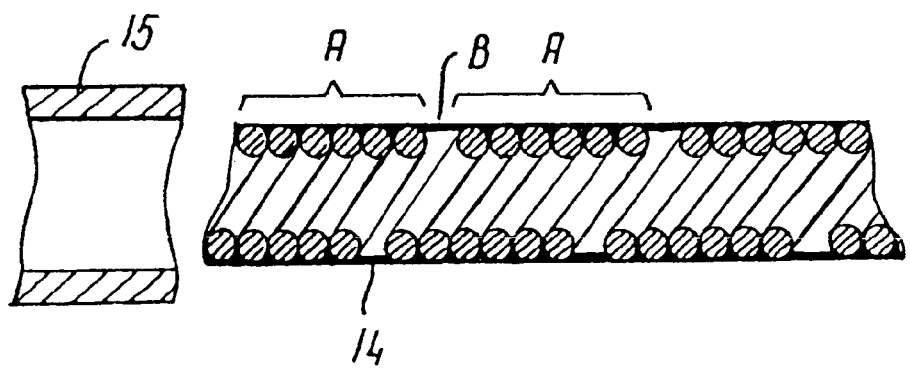
Figure 1A:
Figure 1B:

Referring now to FIG. 3, the wound wires 5 are provided with a sealing coating 14 on the inside, or on the outside or on both, surfaces of the catheter body. The coating is relatively thin and is preferably made of an elastic material which can be hydrophilic. The coating extends along the entire length of the catheter and is typically applied after winding and heat treatment of the catheter body have been completed. As an example, the coating can be of PTFE applied onto the outside surface of the body portion in the same manner as such a coating is traditionally applied onto the exterior of a guidewire. When the coating is to be applied on the external and the internal surfaces of the body portion the catheter length can be dipped briefly into a bath of liquid coating material, which is then allowed to solidify following removal from the bath.

In case it is desirable to use a hydrophilic coating, the coating can comprise a hydrophilic polymer selected from the group comprising polyacrylate, copolymers comprising acrylic acid, polymethacrylate, polyacrylamide, poly(vinyl alcohol), poly(ethylene oxide), poly(ethylene imine), carboxymethylcellulose, methylcellulose, poly(acrylamide sulphonic acid), polyacrylonitrile, poly(vinyl pyrrolidone), agar, dextran, dextrin, carrageenan, xanthan, and guar. The hydrophilic polymers can comprise ionizable groups such as acid groups, e.g., carboxylic, sulphonic or nitric groups. The hydrophilic polymers may be cross-linked through a suitable cross-binding compound. A cross-binder generally comprises two or more functional groups which provide for the connection of the hydrophilic polymer chains. The actually-used cross-binder depends on the polymer system: if the polymer system is polymerized as a free radical polymerization, a preferred cross-binder comprises 2 or 3 unsaturated double bonds.

By making the inventive device primarily of a group or row of two or more wires, which row is helically wound with a pitch roughly corresponding to the aggregate width of the adjacent wires in the row, the wound wires transfer torque and also force components directed in the axial direction of the catheter to the distal end thereof, and this construction is found to give a very high resistance to kinking of the device. When the device is heavily bent the cross-section of the device maintains a circular shape, and the forces transmitted through the helically wound wires have less tendency to be concentrated in the area of the bend. This is a distinct advantage over prior art devices of the type that define a lumen (e.g., catheters and sheaths), which are deformed into oval shape when bent, and thus they are much more prone to kinking. The device surprisingly maintains its capabilities for transferring torque and push when it follows a tortuous path involving two or more loops, probably because of the excellent kinking resistance; and in curved areas the torque and push is mainly transmitted within the device resulting in a favorably low influence on the vascular walls.

Due to the very high flexibility, pushability and torqueability and the ability of the construction of the inventive device to maintain each of these three characteristics even when set in a very tortuous pattern involving two or more tight loops, the device can be of use in very small and distant vessels such as deep brain sites accessed by intracranial catheterization.

If required, the flexibility of the distal portion of a luminal device during advancement along a tortuous path, can be further increased by avoiding the use of a guidewire. The body portion of a catheter, for example, can be maneuvered to the desired prosthesis deployment site like a guidewire because it is made of the multiple wire coils so in terms of maneuverability there is no need for using the catheter in conjunction with a guidewire. However, a guidewire can be used to diminish the action of the catheter tip on the vascular wall because the tip will follow the guidewire when such is advanced in front of the catheter prior to pushing the catheter forward. It is an advantage of the catheter according to the present invention that the wall is primarily made of wires that provide a hard and relatively low-friction or slippery inner surface resulting in low resistance to advancing a member through the lumen of the catheter.

When the catheter is used without a guidewire in a soft tissue region it is preferred that the distal end of the catheter is provided with a buffer member, such as a soft obturator. The buffer member distributes the force from the catheter tip over a large area so that damage to the vascular wall is avoided.

In one embodiment the group or row of wires is made up of from 2 to 12 helically wound wires, preferably of from 4 to 8 helically wound wires. By using several wires their aggregate width can be adapted to correspond to the desired pitch for the given diameter of the device. A row of more than 12 wires would have a tendency to buckle when the wires are helically wound in the common winding operation. For wires of round cross-sectional shape a number of from 4 to 8 wires in the row is preferred, but for flat wires or wires of oval shape two or three wires in a row can be more suitable.

In order to promote uniform and well-defined characteristics of the inventive device along its length the wires in the row can be located closely next to each other so that the mutually contact each other almost continuously and support each other. In this manner a possible deflection of a single wire strand is reduced to a minimum by the others wires in the row. As the wires in the row are wound into a helical course in a common movement there can be an interstice between the turns of the row of wires. The inside surface of an inventive catheter is also more even, which promotes advancing of a central member axially therewithin. The capabilities of torque and push are presumably a result of a kind of mutual interlocking of the individual wire strands in the group or row of wires. If one wire in the row has a tendency to kink or bend heavily under influence of the load applied to the delivery member, the other wires in the row keep said wire in place because they are all extending in a common helical course, which interlocks the wires.

Where the inventive device is a delivery member for an embolization coil, after advancement of the introducer to the desired deployment site, a rotational movement at the proximal end of the delivery member is immediately transmitted into an almost identical rotational movement of the connection means at the distal end (viz., about 1:1 torque transferral). Such an introducer is particularly useful in association with the connection means being designed for detachment by unscrewing from the embolization device, because the rotation of the delivery member during unscrewing will cause only negligible influence on the vasculature, and the embolization device can thus easily be kept exactly at the desired position during detachment, and furthermore there is obtained a very precise control of the detachment when, for example, three turns at the proximal end immediately results in an identical three turn rotation at the distal end of the delivery member.

In an embodiment the wires in said row have a pitch angle in the range of 26° to 76°, preferably a pitch angle in the range of 40° to 65°. Although it is possible to use other pitch angles, angles chosen in these ranges provide a balanced solution to the requirements for the desired high flexibility, high column strength and fine torqueability. The inner range of 40° to 65° is in particular useful for advancing a catheter to very distant, small sized vessels, such as in blood vessels in the brain, whereas the subrange of 35° to 40° is applicable when very high flexibility is a dominant requirement, and the subrange of 70° to 76° is applicable when very high pushability is a dominant requirement. It is of course possible to choose different pitch angles in different segments of the device.

At the time of performing the winding operation of the body portion, the individual wires in the row wound in the helical pattern have preferably a mainly circular cross-section. This facilitates the winding operation because twisting of a wire does not result in disorder in the row.

The sealing coating is preferably elastic. The wires are to a large extent mutually locked in position because several wires are wound in a common movement and thus one wire in the row is kept in place by the other wires in the row, but nevertheless some mutual movement can occur between the wires and in particular between the distal wire in one turn and the proximal wire in the consecutive turn. The sealing coating seals the interstices between the wires so that the catheter wall is leakproof. The elasticity of the sealing coating allows the wires to effect small mutual movements so that the excellent flexibility of the helically wound row of wires is maintained, and the elasticity also allows the catheter wall to stay leakproof when the wires move. The elasticity is a particular advantage when the device is pulled back as the pulling action can tend to elongate the body portion.

It is possible to provide the sealing coating only on the inner surface of the body portion which will result in a device of a very small wall thickness relative to its diameter. If a slightly enlarged diameter is acceptable, the coating can also or as an alternative be placed on the outside of the body portion. The increase in diameter will be relatively modest as the sealing coating can be made thin. The sealing coating provided on the outside of the body portion can, for example, result in no more than a 5 to 15% increase of the outer diameter of the catheter body.

In an embodiment the sealing coating is a low-friction coating, such as polytetrafluoroethylene (PTFE) coating. A low-friction coating applied on the external side of the device wall acts to reduce the forces required to push forward the device inside a larger guiding catheter or a sheath, and a low-friction coating applied on the internal side of the catheter wall acts to reduce the forces required to push forward a guidewire or another member such as a pusher member advanced through the device.

In yet another embodiment the sealing coating is a hydrophilic coating. Such a coating can traditionally be applied to the exterior of a device for reducing the tendency of the device to stick to the vascular wall, but according to the present invention in addition to the lubricating effect of the coating it also effects the sealing of the body portion. The sealing coating is preferably thin and constitutes only a minor part of the wall thickness of the body portion. The thickness of the coating at the middle of the wire can be less than 0.1 mm, and preferably it is less than 0.02 mm.

It is possible to promote the flexibility of the device by machining the wires in said row to a lesser outer diameter, e.g., by grinding, at a region of the device. The region can extend along the whole length of the body portion, so that it is given a very precise outer dimension by the machining. In another embodiment the region is a distal region machined to a tapering shape with decreasing outer diameter in the distal direction causing the device to have an increasing flexibility towards the distal end which promotes the introduction into very diminutive vessels. The reduced cross-sectional area of the wires produced by the machining greatly increases the bending flexibility of the device without sacrificing its ability to transfer torque.

Where the device of the present invention is utilized for delivery of a prosthesis such as a stent, it is preferred that at least in a 30 cm long distal area the delivery system have a maximum outer diameter of 3.0 mm, and suitably less than 2.0 mm. As use of a traditional separate sheet for keeping the prosthesis compressed can be wholly dispensed with because the prosthesis receptacle is in itself capable of keeping the prosthesis in the fully compressed state, the outer diameter of the receptacle and the shaft portion is identical to the maximum outer diameter of the delivery system portion introduced into the vascular system. A maximum diameter of 3 mm in the part of the device advanced through the vascular system allows for straightforward percutaneous introduction by the Seldinger technique and easy navigation through the curves in the larger vessels.

It is preferred that for most other forms of the invention, the device at least in a 30 cm long distal area, have a maximum outer diameter of less than 2.0 mm. A maximum diameter of less than 1.00 mm allows introduction into quite fine and diminutive vessels such as into the external and internal carotid arteries. It is further possible to restrict the maximum outer diameter to at the most 0.75 mm which makes it possible to easily advance the inventive catheter into, for example, the liver or other soft tissue areas, and by keeping the maximum outer diameter below 0.30 mm in a distal end area having a length of at least 10 cm even the most distant vascular regions are accessible and this embodiment of the catheter is excellent as a neuro-microcatheter.

When the inventive medical device is to be an embolization device introducer, it is preferred that at least the distal area have a maximum outer diameter of 1.0 mm. A maximum diameter of 1.0 mm in the part of the embolization device introducer advanced through the vascular system allows for a straightforward percutaneous introduction by the Seldinger technique and easy navigation through the curves in the larger vessels. Coils having the relatively large diameters in the range of 0.7 to 1.0 mm are suitable for embolization in larger vessels, and in particular at locations where the blood flow rate is high, e.g., due to a malformation or trauma. A maximum diameter of 1.00 mm allows introduction into quite fine and diminutive vessels such as into the external and internal carotid arteries.

In a further embodiment the number of wires in said helically wound group or row of wires varies along the length of the device. This can be attained by reducing, during the winding operation, the number of wires in the row. The lower number of wires in the row can be utilized to wind the wires with a larger pitch angle which increases the flexibility of the device. It is preferred that the number of wires diminishes in the distal direction so that the softness of the device increases without any change of material and without bonding together several separate device segments.

When the device has to traverse large lumen vascular paths in order to reach the more difficult small size vascular vessels, the helically wound row of wires can be stiffened in a proximal segment of said body portion by a supplementary tubular member, such as a cannula tubing.

In the following, some examples of catheters are described that are made according to the invention.

Example 1

A catheter was made of a helically wound row of four wires of 0.35 mm wire diameter. The body portion of wound wires had initially an outside diameter of 1.67 mm and an inner lumen of 0.97 mm. A coating of PTFE of a minimum thickness of 0.1 mm was applied onto the inside of the catheter. The catheter was set in a complex curved shape involving three consecutive loops of a loop diameter of 24 mm axially separated by two loops of a loop diameter of 18 mm and a number of further turns representative of a complex vascular structure. Then the body portion of the catheter was manipulated and it proved to be easily pushed forward and retracted as well as easily torqued. Then a guidewire was pushed forwardly in relation to the body portion, and it proved to be easily pushed out past the distal end of the catheter without causing noticeable flexion or movement of the catheter.

Example 2

A catheter was made of a helically wound row of five wires of 0.30 mm wire diameter. The winding of a first segment of the body portion was made with an outside diameter of 1.20 mm and an inner lumen of 0.6 mm. Another segment was made up of a second helically wound row of four wires of 0.15 mm wire diameter. This segment had a length of 20 cm and an outside diameter of 1.20 mm and an inside diameter of 0.9 mm. The segments were joined by laser welding. The catheter body was provided with a flexible coating on its outside. The catheter was advanced through a complex curved vascular system involving several consecutive retrograde turns in vessels having a lumen of only 2 mm and less. Then the catheter was torqued and moved both forwardly and backwardly without any problems.

Example 3

A catheter was made of a first helically wound row of eight wires of 0.075 mm wire diameter. The winding was made with an outside diameter of 0.25 mm and an inner lumen of 0.1 mm. The body portion had a length of 160 cm and was coated with a hydrophilic material of polyacrylamide on its outside surface. When tested the catheter shows no problems. After placing the catheter in a very complex pattern involving several sharp turns (see an example in FIG. 9), a guidewire could be advanced with only very low friction, and after removal of the guidewire, a fluid could be injected through the catheter without leakage through the coating.

When the catheter is to be introduced into the vascular system there is firstly established a percutaneous puncture site, e.g., by the Seldinger technique, or an existing puncture site is used. Then the body or shaft portion of the catheter is inserted through the cannula, sheath or hemostatic valve at the puncture site and the catheter is advanced and navigated through the vascular system to the treatment site or the prosthesis deployment site. Due to the very high flexibility, pushability and torqueability of the catheter it can be advanced to the site without use of a guidewire, or a sheath to negotiate the sharp curves in the path. When large lumen vessels are to be traversed in order to enter the vasculature near the target site, it can be an advantage to stiffen the proximal portion of the catheter by inserting it through a cannula 14 (FIG. 3), a tubing or another kind of a more rigid structure.

The catheter according to the invention can be used as a traditional catheter, and it can also be used as a sheath which has normally a shorter length than a traditional catheter.

Individual features of the various embodiments can be combined into further embodiments according to the present invention. It is possible to effect the sealing coating as a multilayer coating, e.g., comprising a primer-coating and a top-coat where the primer-coating is chosen to provide a strong bonding to the wires, and the top-coat provides the sealing action and can be a hydrophilic slippery coating providing a low friction surface.

Figure 10:
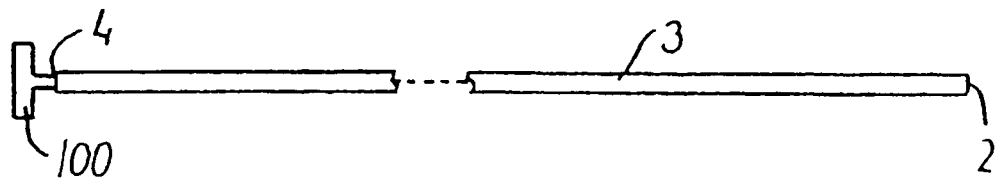
FIG. 10 is an illustration of a device of the present invention used in a delivery system having a central member that serves as a pusher.
Figure 11:
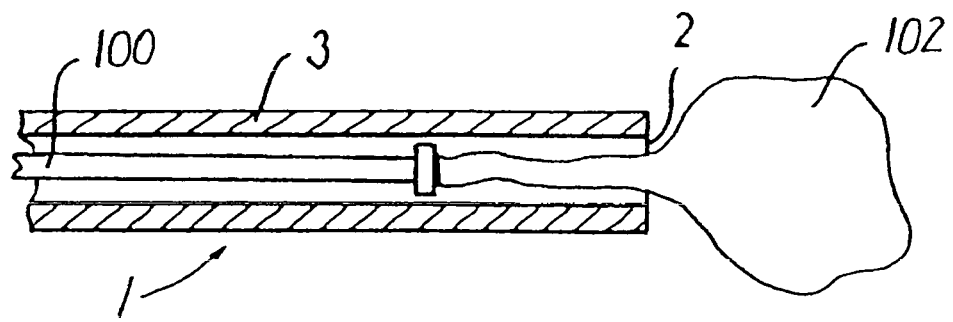
FIGS. 11 and 12 are enlarged views of central members of FIG. 10 being advanced out of the distal end of the catheter.
Figure 12:
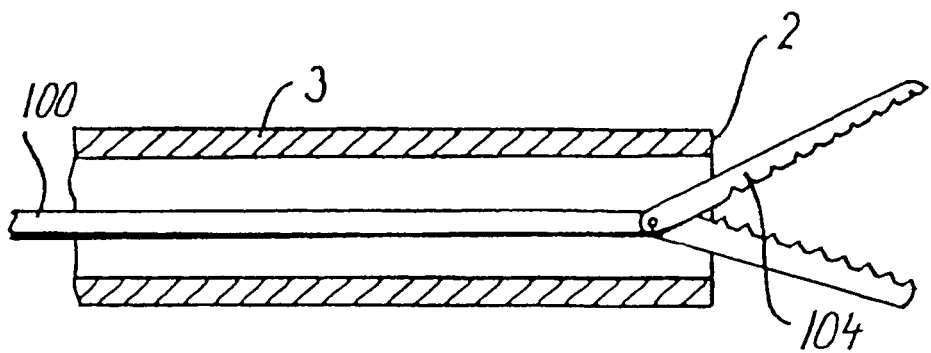

A catheter system is illustrated in FIG. 10 to include a central member 100 such as a pusher, and a catheter 1 having a distal end 2 and a body portion 3 extending from the distal end to a proximal end 4, the catheter being similar to catheter 1 of FIG. 1. The central member may be used to block the distal opening during inflation of a balloon of a balloon dilatation catheter for percutaneous transluminal coronary angioplasty. The catheter system can also be for placing the central member in the vascular system. To give some examples, the center member can include (or can be) an embolization means in the form of a sack 102 containing several occlusion coils, as shown in FIG. 11. It also can be a stent for expansion on a balloon, or it can be a sensor body for measuring pressure or temperature or the composition of blood, or it can be a physical shunt member. It also can be or include a retrieval wire or a forceps 104, as shown in FIG. 12 used to retrieve another member from a vascular site, or it can be a central member of some other kind.

Following are three examples of catheter systems made according to the invention.

Example 4

A catheter was made in accordance with the catheter of Example 1 and deployed in the complex vascular structure described therein. Then a bag 102 with four occlusion coils was pushed forward by the pusher 100 (FIG. 10) until it discharged through the opening at the distal end 2, as shown in FIG. 11. There was no noticeable sticking of the bag 102 against the inside surface of the catheter.

Example 5

A catheter was made in accordance with the catheter of Example 2 and provided with a PTFE coating on its outside surface. The catheter was advanced through a complex curved vascular system involving several consecutive, retrograde turns in vessels having a lumen of only 2 mm and less.

Then a pair of forceps 104 was advanced through the catheter as shown in FIG. 12, and activated to grab the desired item, such as a kidney stone, and retracted through the catheter lumen.

Example 6

A catheter was made having the wire structure and dimensions of the catheter in Example 3. The body portion was uncoated, and when tested the catheter showed no problems. After placing the catheter in a very complex pattern involving several sharp turns (see an example in FIG. 9) a guidewire could be advanced with only very low friction, and after removal of the guidewire, central members in the form of fluid injected embolization coils were delivered through the catheter.

Shown in FIGS. 13 to 18 is a delivery system according to the present invention, for use in the delivery of a prosthesis to a treatment site in the vasculature. The prosthesis may be of the radially compressible, self-expandable type such as a stent, a stent graft, a valve member or a filter, and may be formed of shape memory alloy. When the delivery system has been maneuvered to the desired location, the prosthesis is discharged by application of a pushing force against the proximal end of the prosthesis relative to the delivery system by means of a pusher member; alternatively, the prosthesis may be discharged by being held by a trigger wire against proximal movement as the surrounding catheter or sheath is pulled proximally.

Figure 13:
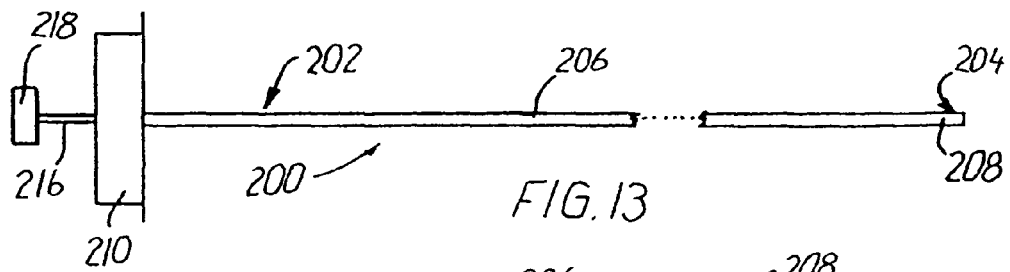
FIG. 13 is an illustration of a delivery system of the present invention, for delivery of a prosthesis such as a stent.

Delivery system 200 in FIG. 13 includes a delivery device 202 having a distal end 204 and a shaft portion 206 extending between a prosthesis receptacle 208 at the distal end and a proximal mounting member 210 fixedly mounted to the shaft portion. The shaft portion is made of a first helically wound multiple filament row of wires 212 and it has a central longitudinally extending lumen 214.

The delivery system 200 further comprises a pusher member 216 which can be inserted through the lumen 214. A handle or pin vise 218 is mounted on the pusher member for pushing it forwardly in the distal direction when a prosthesis 220 located in receptacle 208 is to be released from the introducer device by being pushed out of receptacle 208. Pin vise 218 and mounting member 210 can be parts of a unitary control device to be manually actuated when the prosthesis has been introduced and positioned at the desired vascular site.

At the distal end of the pusher member 216 an engagement means 222 can act on the prosthesis 220. The engagement means can be for example a plate of a dimension fitting into receptacle 208 and abutting the proximal end of the prosthesis so that the plate pushes the prosthesis out of the receptacle when the pusher member is pushed forwardly. The engagement means can also be designed as an elongate member that extends coaxially inside the radially compressed prosthesis and engages the prosthesis at several locations along the length thereof so that the prostheses is partly pulled, partly pushed out of the receptacle. These engagement points or areas can be effected by radial projections, hooks, ridges, or another kind of engagement means such as a high friction material. This can be an advantage if the prosthesis has an extensive length, and in particular if it has a construction having a tendency to buckle when pushed upon.

By the term "prosthesis receptacle" is meant any structure or region near or at the distal end of a delivery device where a radially compressible tubular prosthesis is carried during maneuvering of the delivery device and prosthesis within a body lumen. The prosthesis receptacle 208 can be made of a length of tubular material that is flexible in itself or is made flexible by incisions or due to its construction, such as a construction of wound or braided wires. If the prosthesis is rather short in length or is for deployment in a large sized vessel of a rather straight shape, such as in the aorta, the receptacle need not be flexible and can be made out of a stiff tubular member.

Figure 18:
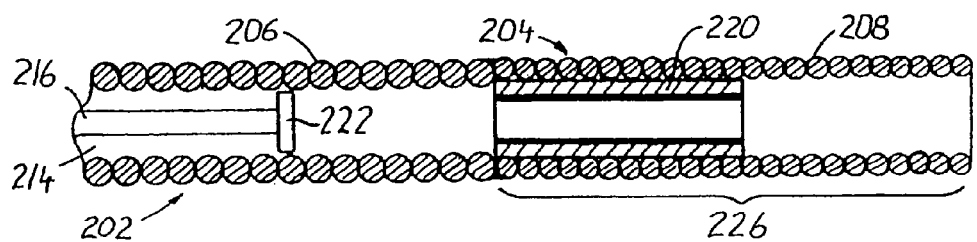

The length of the prosthesis receptacle 208 is at least of the same size as the length of the loaded prosthesis 220. However, other lengths are also possible As depicted in FIG. 18, the receptacle 208 can have a length that is considerably longer than the loaded prosthesis 220, so that the prosthesis can be loaded into a position at the proximal end of the receptacle leaving empty a distal length of the receptacle. This free distal length will not be stiffened by the presence of the loaded prosthesis and will consequently be very soft and flexible. The length can for example by chosen so that the free distal length is in the range of from 5 to 150 mm, preferably in the range of 10 to 50 mm.

Figure 14:
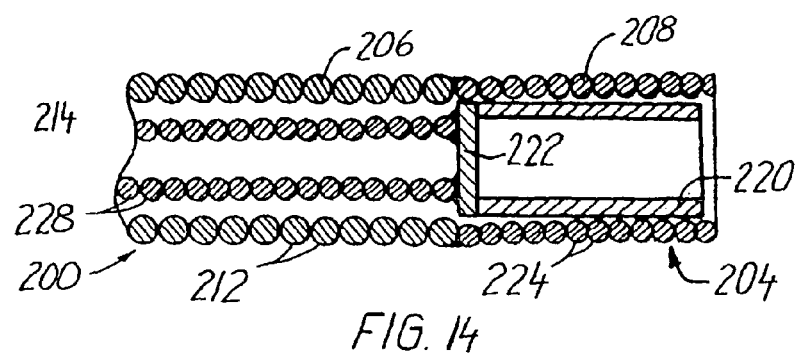
FIGS. 14 to 18 are enlarged partial views in longitudinal section of various embodiments of the delivery system of FIG. 13.

In a preferred embodiment, the prosthesis receptacle 208 is made of a second helically wound multiple filament row of wires 224. As depicted in FIG. 14, the second row of wires 224 can be made independently of the first row of wires 212 and in different dimensions or different materials than the first row of wires, and the receptacle 208 is then fixed in axial extension of the first row of wires, e.g., by laser welding, soldering bracing, or mechanical locking such as press-fitting into the lumen of the shaft portion, or binding with threads or suture. An alternative embodiment is depicted in FIGS. 15 and 16 where prosthesis receptacle 208 is made integral with shaft portion 206 by using a distal segment 226 of said first row of wires 212 as the receptacle.

Figure 15:
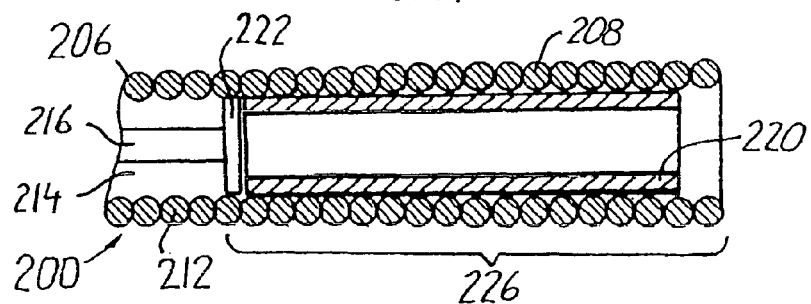

In the embodiment of FIG. 15, the inner lumens in the shaft portion 206 and in receptacle 208 are of even size which brings the advantages of being able to load prostheses of various lengths in one and the same delivery system and of being able to lead from the proximal end of the delivery device a pusher member having a solid engagement means 222 of a diameter that is only slightly less than the diameter of the inner lumen 214.

Figure 16:
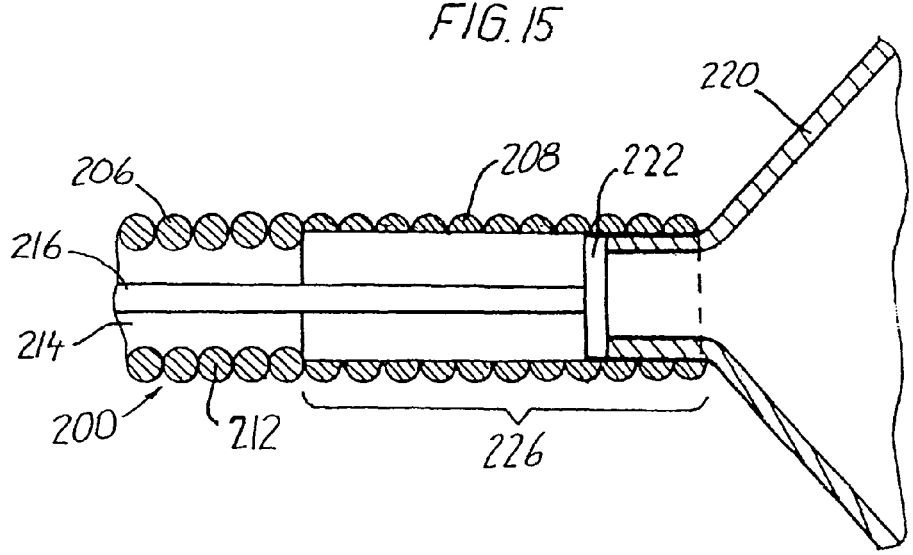

In the embodiment of FIG. 16, the pusher member 216 is inserted from the distal end of the shaft portion prior to leading the prosthesis 220 into receptacle 208. This allows the engagement means 222 to be of a larger diameter than the lumen 214 of shaft portion 206.

In the embodiment of FIG. 18, the radially compacted prosthesis 220 projects radially inwards beyond the step in inner lumen diameter at the transition between receptacle 208 and shaft portion 206. Consequently, it is possible to use a pusher member 216 having an engagement member 222 of less diameter than lumen 214 and yet push the prosthesis out of receptacle 208 by its pressing against the proximal end of the prosthesis.

The shaft of the pusher member 216 can be of a small diameter solid wire or rid as depicted in FIG. 15 or it can be made of a third helically wound multiple filament row of wires 228 as depicted in FIG. 14. The receptacle 208 in the embodiment of FIG. 16 is made by machining the inside of the wound wires 226 to a larger lumen. This can for example by done by spark erosion or grinding. In the latter case, the distal end portion of the wound wires are placed in a retaining ring (not shown) that is longitudinally displaceable with respect to a coaxially mounted grinding wheel.

Figure 17:
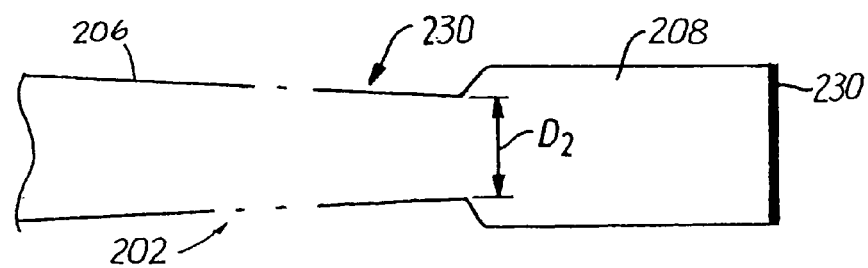

A grinding procedure can also be used to produce a tapered section 230 in shaft portion 206 (seen in FIG. 17). The taper can extend along a substantial length of the shaft portion. In the tapered section the outer diameter of the delivery device 202 diminishes to diameter D2. Due to the taper the delivery device obtains a gradually increasing transverse flexibility and a higher softness, but torque is nevertheless surprisingly transferred fully to the receptacle 208. As an alternative or supplement to grinding, the shaft portion 206 can be composed of several portions in which the wires of each portion have mutually different diameters and cross-sectional areas.

Preferably, the distal tip of the delivery system is provided with marker means 230 for making it radiopaque, e.g., by a gold or platinum plating, or by soldering, brazing or laser welding a radiopaque member onto the distal tip (FIG. 17). The marker 230 promotes precise positioning of the prosthesis at a treatment site in the vasculature.

For some applications it is desirable to deploy a prosthesis that has been provided with an active substance, such as a cell growth inhibitor. The active substance can have such a short shelf life that it needs to be applied to the prosthesis immediately prior to deploying the prosthesis. This can be done by dipping the distal end of the delivery device, viz., the prosthesis in the receptacle, into a fluid of active substance.

Following are some examples of delivery systems made according to the invention:

Example 7

A delivery device was made of a first helically wound row of four wires of 0.35 mm wire diameter. The shaft of wound wires had initially an outside diameter of 1.67 mm and an inner lumen of 0.97 mm. The receptacle was made up of a second helically wound row of four wires of 0.20 mm wire diameter. The receptacle had a length of 37 mm and initially an outside diameter of 1.70 mm and an inside diameter of 1.3 mm. A radially compressed stent was arranged inside the receptacle. The loaded stent had a length of 35 mm and was recessed a little in relation to the distal end of the receptacle. The pusher member was made of a third helically wound row of four wires of 0.28 mm wire diameter and a shaft outer diameter of 0.91 mm. A plunger element or an engagement member was located on the distal end of the shaft. The shaft and the receptacle of the delivery device was ground to a common outer diameter of 1.5 mm (4.5 French). In its fully self-expanded state the stent had an outer diameter of 8 mm. The delivery device was set in a complex curved shape involving three consecutive loops of a loop diameter of 20 mm axially separated by two loops of a loop diameter of 15 mm and a number of further turns representative of a complex vascular structure. Then the shaft of the delivery device was manipulated and it proved to be easily pushed forwardly and retracted as well as easily torqued. Then the pusher member was pushed forwardly in relation to the shaft portion, and the stent was easily pushed out of the receptacle without causing noticeable flexion or movement of the delivery device.

Example 8

A delivery device was made of a first helically wound row of five wires of 0.30 mm wire diameter. The winding of the shaft was made with an outside diameter of 1.20 mm and an inner lumen of 0.6 mm. The receptacle was made up of a second helically wound row of four wires of 0.15 mm wire diameter. The receptacle had a length of 60 mm and an outside diameter of 1.20 mm and an inside diameter of 0.9 mm. A radially compressed prosthesis was arranged inside the receptacle. The loaded prosthesis had a length of 20 mm and was positioned at the proximal end of the receptacle with a 40 mm very soft free distal receptacle end. The pusher member was made of a single 0.35 mm diameter wire rod that carried an engagement member at its distal end. In its fully self-expanded state the prosthesis had an outer diameter of 3 mm. The delivery device was advanced through a complex curved vascular system involving several consecutive, retrograde turns in vessels having a lumen of only 2 mm or less. Then the pusher member was pushed forwardly in relation to the shaft portion, and the stent was easily pushed out of the receptacle in a well-controlled manner.

Example 9

A combined receptacle and distal shaft segment of a delivery device was made of a first helically wound row of eight wires of 0.075 mm wire diameter. The winding was made with an outside diameter of 0.25 mm and an inner lumen of 0.1 mm. The combined receptacle and distal shaft segment had a length of 12 cm. A prosthesis was compressed radially to an outer diameter of 0.07 mm and was pushed into the receptacle. The loaded prosthesis had a length of 10 mm and was positioned in the receptacle with its proximal end 25 mm from the distal receptacle end. The pusher member was made of a single 0.08 mm diameter solid wire rod. The pusher member was used to push the stent out of the receptacle.

Shown in FIGS. 19 to 27 is a delivery system for an embolization coil, made according to the present invention. A delivery system 300 has a length in the range of 50 to 250 cm and a diameter in the range of 0.08 to 2.0 mm, depending on the relevant field of application. The delivery system utilizes a delivery member 302 within an introducer 304, and in a distal section 306 the delivery member has a connection means 308 for an embolization device 310.

Figure 19:
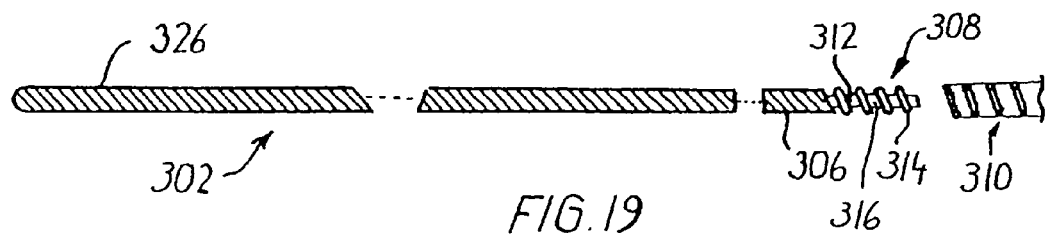
FIG. 19 depicts a partial view of a delivery member of an embolization device introducer according to the present invention.

The delivery system may utilize any of a number of kinds of connection means 308, among which are: an electrolytically erodable means, a heat erodable means, a latch, a coupling, a threading coil, a thread, a deflatable balloon, and a hydraulically or pneumatically activated gripper means. As shown in FIG. 19, the delivery member 302 preferably has in its distal section 306 a central core 312 with a blade-shaped portion, and the connection means 308 is a threading coil 314 which is fixed to the central core at least at the edges of the blade-shaped portion. The blade-shaped portion carrying the threading coil is much more flexible and easy to bend in the thickness direction of the blade than in the direction of the width where the blade dimension is the largest. The blade-shaped portion is a distal end portion 316 of the central core 312 and if it is subjected to a torque, the central core twists. When the delivery wire is advanced and has to pass through a curvature, the blade-shaped portion touches the inner wall of the lumen and is subjected to a torque until the blade-shaped portion has turned itself with the direction of width transverse to the curvature. The result is that the bending occurs in the thickness direction which is most flexible. The fixation of the threading coil 314 at the edges provides control of the positioning of the threads so that the unthreading of the embolization device 310 is very smooth-running.

The connection means 308 can be made of radiopaque material in order to be discerned on an image screen by the radiologist or neuroradiologist that introduces the detachable embolization device 310 into the vascular system of a patient, but in order to be seen clearly the radiopaque area ought to have relatively large dimensions. This can be obtained by positioning a radiopaque marker at a predefined first distance, such as about 3 to 3.5 cm, proximal to the distal termination of the connection means 308. In this embodiment, the connection means in itself need not be radiopaque, because the marker is clearly seen and the radiologist is aware that the embolization device is positioned said first distance ahead of the marker.

Figure 23:
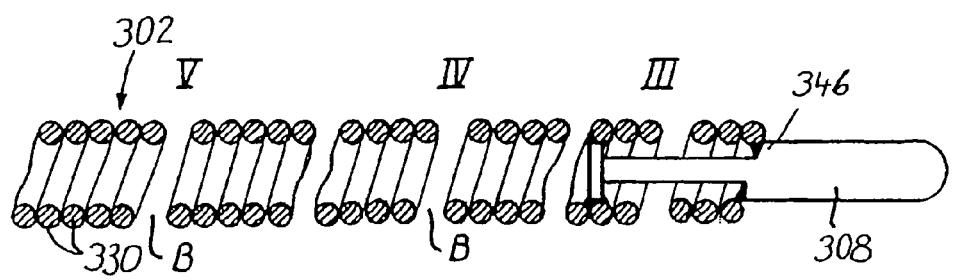
Figure 24:
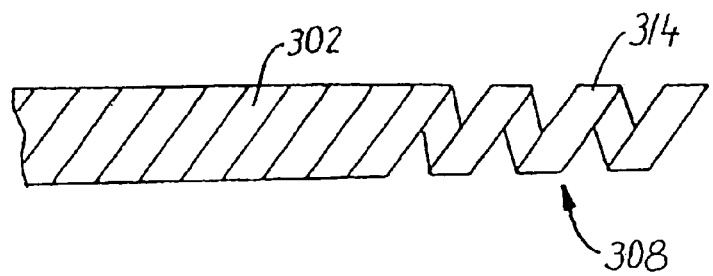
FIG. 24 is an enlarged view of a coil connection means of FIG. 19.

In the following description of several embodiments, the same numerals are used to denote features of the same kind. In one embodiment the connection means 308 comprises a central core 312 of stainless steel, nitinol, or another suitable material and a threading coil 314. The central core 312 has at its distal end section 316 a blade-shaped portion with a blade thickness and a blade width, which is more than twice as large as the blade thickness. The threading coil 312 is fixed onto the blade-shaped portion, e.g., by soldering, welding, brazing or gluing at joints 346 (as seen in FIG. 23). The threading coil wire can be of stainless steel and can have a wire diameter in the range of 0.02 to 0.12 mm, typically a diameter of about 0.06 to 0.075 mm. The wire is set with a pitch corresponding to or being larger than twice the thickness of the wire so that a mating threading in the proximal end of the detachable embolization device 310 can be threaded into and out of threading coil 314, as shown in FIG. 24. The outer diameter of the threading coil can, for superselective use, be in the range of 0.08 to 1.0 mm, and typically from 0.20 to 0.45 mm.

Other embodiments of the connection means 308 include a connecting area, which is eroded away by applying current or head when the embolization device 310 is positioned at the desired site, or a latch or a coupling providing a geometrical locking, such as a bayonet coupling, two mating parts held together by a thread that can be pulled out for detachment of the embolization device, or a deflatable balloon positioned inside a tubular proximal end area of the embolization device 310. Other embodiments of threads can also be used, such as spaced ball-like enlargements on the central member, a helix-shaped groove cut into a cylindrical or conical distal end part on delivery member 302. These kinds of connection means are well known in the art, e.g., from EP-A-0 720 838; U.S. Pat. No. 5,217,484; WO 94/06503; WO 94/06502; WO 94/00104; and EP-A-0 717 969. In FIG. 23 such a connection means 308 is shown in a general manner, and an activation member 318 is shown to extend inside the delivery member 302. The activation member can be, for example, the above mentioned thread to be pulled out, an optical fiber, an electrical wire, and so forth.

The embolization device 310 can be a Gianturco stainless steel coil of traditional design, or coils with a regular helical shape or irregular coil shape as described in U.S. Pat. Nos. 4,994,069; 5,122,136; WO 93/06883; WO 94/11051; WO 94/07560; WO 94/10936; WO 95/25480; DE-295 18 932-U1; WO 96/18343; EP 0 623 012 or the embolization device can be a random matrix shape as described in U.S. Pat. No. 4,994,069 and WO 94/09705. The embolization device can also be of a regular linear shape as described in WO 98/09570, which is hereby incorporated into the present description by reference. The embolization device can also be called an occlusion device.

Figure 20:
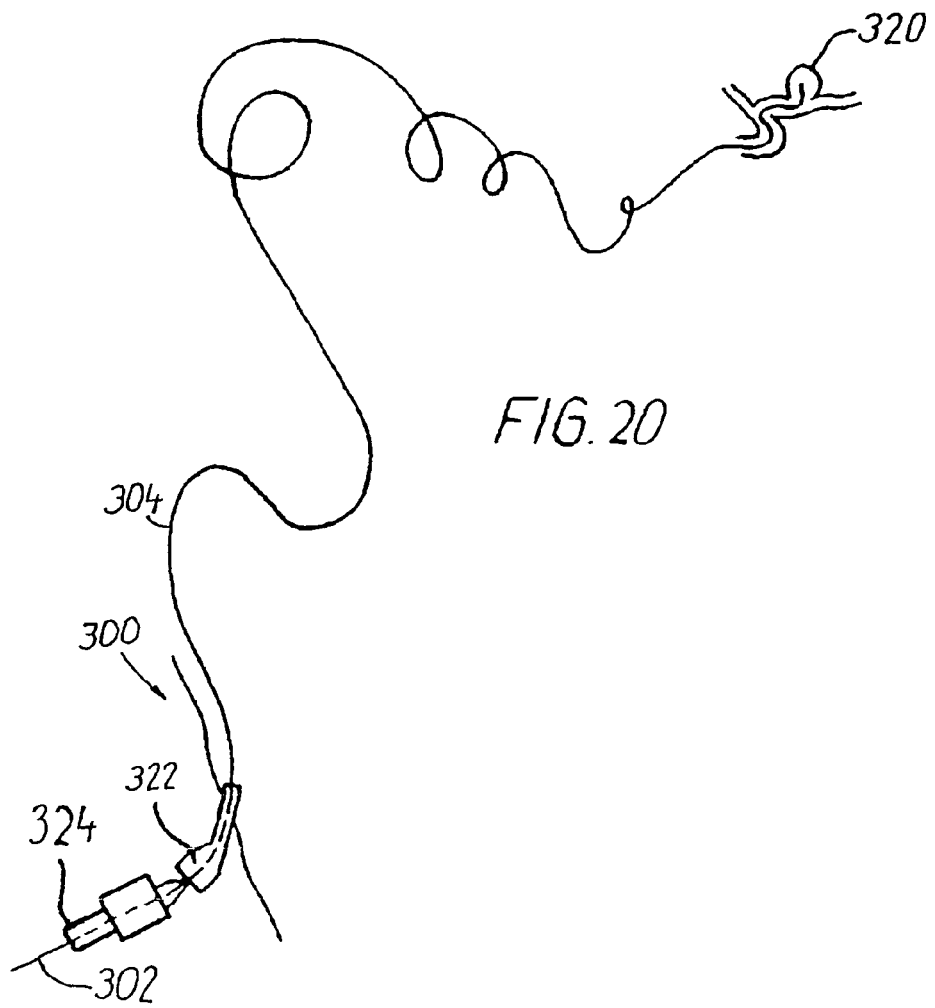
FIG. 20 is a sketch of the introducer of FIG. 19 ready for disengaging an embolization device.
Figure 21:
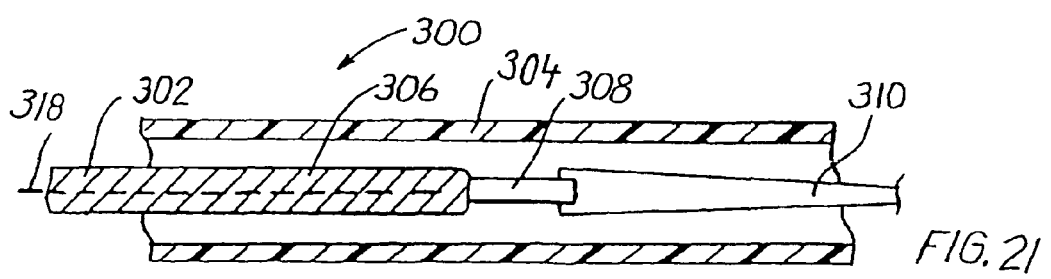
FIG. 21 is an enlarged illustration of the distal end of the delivery member of FIG. 20 with an embolization device during placement in a catheter.

Referring now to FIGS. 20 and 21, placement of the embolization device 310 in an aneurysm 320 will be described. A catheter is introduced percutaneously through a fitting 322 by the Seldinger technique and advanced transluminally in a well known manner along a suitable path until the distal end of the catheter is located in the neck of the aneurysm 320. Then an introducer 304 with the embolization device 310 mounted on the delivery member 302 is inserted into the catheter and pushed forwardly until the embolization device is pushed out of the catheter and is in the desired deployment position in aneurysm. So positioned, the delivery member extends along a complexly curved path. Then the embolization device is released from connection means 308. This can be done, for example, by activating member 318 or by rotating the proximal end of the delivery member with the aid of a pin vise 324 which is fixed onto a proximal section 326 of delivery member 302.

Referring now to FIGS. 22 to 27, wires 330 are wound by a winding operation in a manner such as that described with respect to FIG. 2. The winding operation can be effected so that the windings are touching each other, but preferably it is performed so that a slight interstice B is present between the turns (FIG. 23). The interstices facilitate bending of the body portion in tight turns of the vasculature (FIG. 20). The size of the pitch angle depends on the diameter of the wires, the diameter of the delivery member 302 and the number of wires in the sequence, group or row. The most preferred pitch angle for the delivery member is in the range of 40° to 65°. However, the combination of torque-transferral, pushability and transverse flexibility is normally well-balanced for pitch angles in the range of 50° to 68°. The diameter of the wire is typically in the range of 0.03 to 0.75 mm, and preferably in the range of 0.15 to 0.45 mm.

Figure 22:
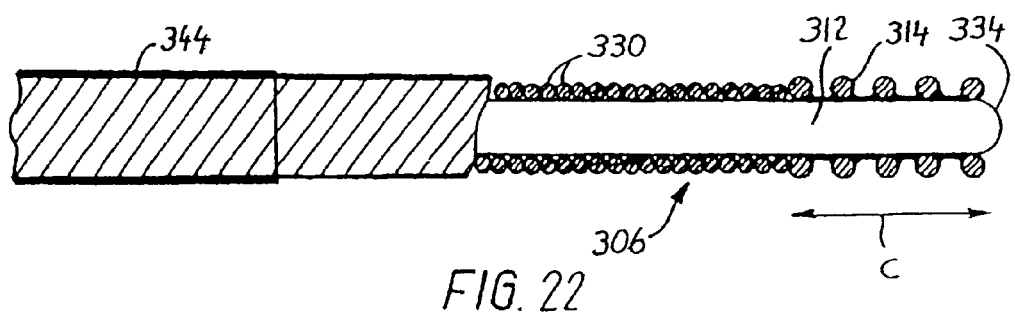
FIGS. 22 and 23 are partial view of the delivery members of other embodiments of embolization device introducers.

In order to make the tip portion of the delivery member more visible on a screen, it is desirable to use some kind of radiopaque marker 332 or radiopaque material, such as platinum or gold. It can be of annular shape and be located at a predetermined distance c from the distal end 334, as shown in FIG. 22. The marker can be of platinum wire inserted into delivery member 302 in distal extension of wires 330, or it can be a separate member such as a platinum or gold ring. A catheter 336 used when advancing the introducer 304 can also have a radiopaque marker 338 located at such a distance from the distal end 340 of the catheter that the embolization device 310 is in position for release when the marker 332 has been advanced to be positioned at marker 338.

In the embodiment illustrated in FIG. 23 the number of wires 330 in portions of the length of the delivery member 302 varies along the length. During the winding operation the number of wires in the group is reduced one by one at the points where individual portions having a constant number of wires have obtained their desired lengths. The segments marked V, IV and III have five, four and three wires, respectively, in the group. Each time a wire is left out of the group, the pitch gets shorter and the pitch angle grows resulting in an even more flexible consecutive segment. The advantage of this embodiment is that the wires extending into the distal end segment are continuous from the distal end to the proximal end of the delivery member, thus avoiding any need for joining the various portions. It is possible to secure the thread ends of the discontinuous wires onto the other wires, such as by welding, soldering and so forth.

The delivery member can be made with uniform diameter throughout its length. Incase the delivery member is to have diminishing diameter toward the distal end, a prefabricated delivery member of uniform diameter and be ground to the desired dimensions. As an alternative or supplement to grinding, the delivery member can be composed of several segments in which the wires have mutually different diameters and cross-sectional areas, as described with respect to FIG. 5.

Figure 25:
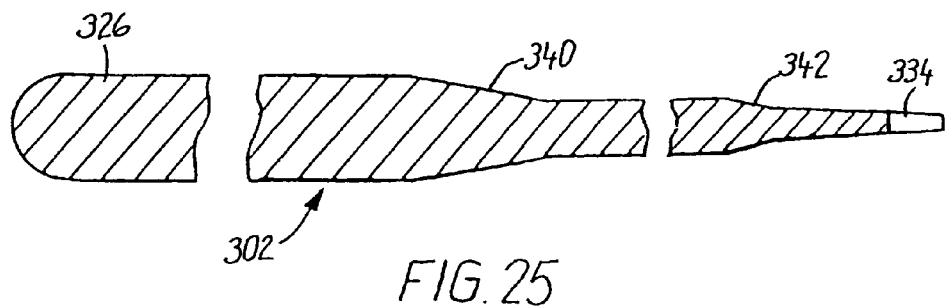
FIGS. 25 and 26 are views of different embodiments of embolization device introducers providing increased flexibility in the distal end area of the delivery member.
Figure 26:
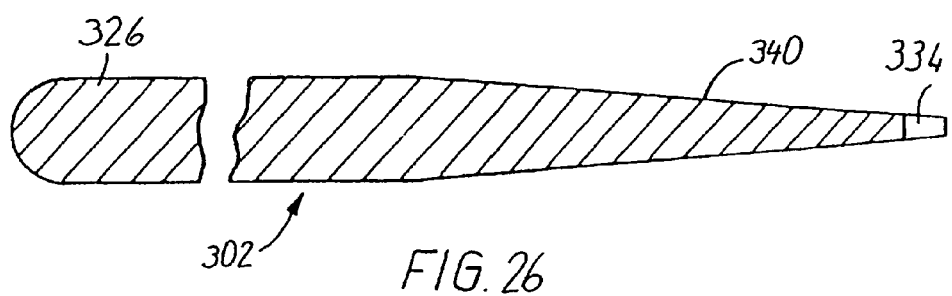
Figure 27:
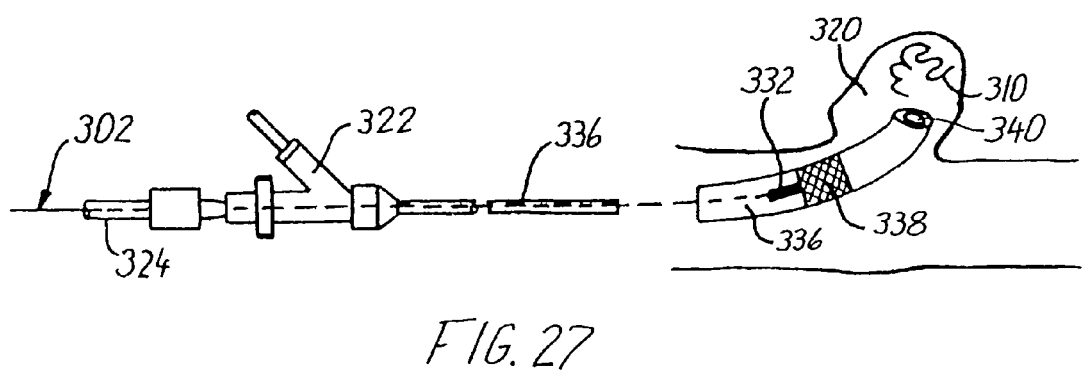
FIG. 27 illustrates delivering an embolization device by the embolization device introducer of FIG. 19.

As illustrated in FIGS. 25 and 26, a grinding procedure can also be used to produce one or more tapered segments 340, 342 in delivery member 302. The taper can extend along a substantial length of the delivery member to produce a gradually increasing flexibility. In the tapered segments, the outer diameter of the delivery member 302 diminishes toward the distal end 334. Due to the taper or tapers, the delivery member obtains a gradually increasing transverse flexibility and a higher softness, but column strength and torque are nevertheless surprisingly transferred to the distal end.

In the embodiment of FIG. 22, the wound wires 330 are provided with a low-friction coating 344 on the radially outwardly facing surface of delivery member 302. The coating is relatively thin and is preferably made of an elastic material which can by hydrophilic. The coating extends along part of or along the entire length of the delivery member and is typically applied after winding and heat treatment of the delivery member have been completed. As an example, the coating can be of PTFE applied onto the outside of the body portion in a traditional manner.

The helically wound row of wires in the delivery member makes it possible to manufacture the connection means as an integral part of the delivery member. This can be done by removing one or several of the wires in the distal end portion of the delivery member. The wires are very diminutive so that they can be cut, for example, by a laser beam or manually with a tool under a microscope. If required, a thread cutter tool or a thread shaping tool can be used to set the remaining wire or wires with the desired pitch corresponding to the pitch on the mating coupling member on the embolization device. The resulting unitary delivery member has in its distal end only the wires which extend toward the proximal end.

Following are several examples of delivery members made according to the present invention:

Example 10

A delivery member was made of a helically wound row of four wires of 0.30 mm wire diameter. The delivery member had initially an outside diameter of 0.90 mm. The delivery member was set in a complex curved shape involving three consecutive loops of a loop diameter of 24 mm axially separated by two loops of a loop diameter of 18 mm and a number of further turns representative of a complex vascular structure. Then the proximal section of the delivery member was manipulated and it proved to be easily pushed forward and retracted as well as easily torqued.

Example 11

A delivery member was made of a helically wound row of five wires of 0.25 wire diameter. The winding of a first segment of the delivery member was made with an outside diameter of 0.80 mm. Another segment was made up of a second helically wound row of four wires of 0.15 mm wire diameter. This segment had a length of 20 cm and an outside diameter of 0.45 mm. The segments were joined by laser welding. The delivery member was provided with a coating on its outside surface. The delivery member was advanced through a complex curved vascular system involving several consecutive, retrograde turns in vessels having a lumen of only 2 mm and less. Then the delivery member was torqued and moved both forwardly and backwardly without any problems.

Example 12

A delivery member was made of a first helically wound row of eight wires of 0.075 mm wire diameter. The winding was made with an outside diameter of 0.25 mm. The delivery member had a length of 160 cm. When tested, the delivery member showed no problems. After placing the delivery member in a very complex pattern involving several sharp turns, the distal end could be rotated in a 1:1 relationship with a rotation of the proximal end of the delivery member.

What is claimed is:

1. A delivery system comprising:
a delivery device with a distal end and a shaft portion with a lumen extending in a longitudinal direction from a proximal end and toward the distal end, a self-expandable prosthesis arranged in a receptacle at the distal end of the delivery device, and a pusher member arranged in the lumen of said delivery device to cause relative axial movement of the self-expandable prosthesis with respect to the delivery device,
said shaft portion of said delivery device comprising a first helically wound multiple filament row of from four to eight wires of circular cross-section closely adjacent to each other, wherein said row of wires has a pitch angle in the range of 40° to 65°, the wires being provided with a low-friction sealing coating of elastic material on at least a radially outwardly facing surface, the sealing coating having a thickness at the middle of each of the wires of less than 0.1 mm,
said receptacle comprising a second helically wound multiple filament row of from two to twelve wires of circular cross-section closely adjacent to each other, wherein said row of wires has a pitch angle in the range of 26° to 76°,
said pusher member comprising a third helically wound multiple filament row of from two to twelve wires of circular cross-section closely adjacent to each other, wherein said row of wires has a pitch angle in the range of 26° to 76°, and
one of a radially inwardly facing surface of said delivery device and a radially outwardly facing surface of said pusher member being provided with a low-friction sealing coating of elastic material.

2. The delivery system of claim 1, wherein the receptacle is a connection extension that includes at least one helically wound wire of a different cross-section than any one wire of the row of wires extending from the distal section to the proximal section.

3. The delivery system of claim 2, wherein the connection extension for detachably mounting of an embolization device includes a threading coil for threading engagement with the embolization device.

4. The delivery system of claim 2, wherein the connection extension for detachably mounting of an embolization device is configured to be electrolytically erodible.

5. The delivery system of claim 2, wherein the connection extension for detachably mounting of an embolization device is configured to be heat erodible.

6. The delivery system of claim 2, wherein the connection extension for detachably mounting of an embolization device includes a threading coil for threading engagement with the embolization device.

7. The delivery system of claim 2, wherein the distal section of the delivery member includes a radiopaque material.

8. The delivery system of claim 7, wherein the radiopaque material is spaced a predetermined distance from a distal end of the connection extension for detachably mounting of an embolization device.

9. The delivery system of claim 7, wherein the radiopaque material is at least a portion of the connection extension for detachably mounting of an embolization device.

* * * * *

UNITED STATES PATENT AND TRADEMARK OFFICE
CERTIFICATE OF CORRECTION

| | | |
|---|---|---|
| PATENT NO. | : 8,721,625 B2 | Page 1 of 1 |
| APPLICATION NO. | : 11/314541 | |
| DATED | : May 13, 2014 | |
| INVENTOR(S) | : Klint | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1476 days.

Signed and Sealed this
Twenty-eighth Day of July, 2015

Michelle K. Lee
*Director of the United States Patent and Trademark Office*